United States Patent
Wang et al.

(10) Patent No.: US 12,000,916 B2
(45) Date of Patent: Jun. 4, 2024

(54) SIMULTANEOUS EMISSION-TRANSMISSION TOMOGRAPHY IN AN MRI HARDWARE FRAMEWORK

(71) Applicant: Rensselaer Polytechnic Institute, Troy, NY (US)

(72) Inventors: Ge Wang, Loudonville, NY (US); Lars Arne Gjesteby, Cohasset, MA (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 900 days.

(21) Appl. No.: 17/279,400

(22) PCT Filed: Mar. 13, 2019

(86) PCT No.: PCT/US2019/022002
§ 371 (c)(1),
(2) Date: Mar. 24, 2021

(87) PCT Pub. No.: WO2019/178195
PCT Pub. Date: Sep. 19, 2019

(65) Prior Publication Data
US 2021/0389399 A1 Dec. 16, 2021

Related U.S. Application Data (60) Provisional application No. 62/686,727, filed on Jun. 19, 2018, provisional application No. 62/642,645, filed on Mar. 14, 2018.

(51) Int. Cl.
G01R 33/48 (2006.01)
A61B 6/00 (2006.01)
(Continued)

(52) U.S. Cl.
CPC ............ G01R 33/481 (2013.01); A61B 6/037 (2013.01); A61B 6/4258 (2013.01);
(Continued)

(58) Field of Classification Search
None
See application file for complete search history.

(56) References Cited

U.S. PATENT DOCUMENTS

| | | | |
|---|---|---|---|
| 5,338,936 A | 8/1994 | Gullberg et al. | |
| 5,376,795 A | 12/1994 | Hasegawa et al. | |

(Continued)

FOREIGN PATENT DOCUMENTS

| | | |
|---|---|---|
| GB | 2527755 A | 1/2016 |
| WO | 2010027777 A2 | 3/2010 |

OTHER PUBLICATIONS

International Search Report and The Written Opinion of the International Searching Authority, International Application No. PCT/US2019/022002, dated May 15, 2019.

(Continued)

*Primary Examiner* — Jonathan Cwern
(74) *Attorney, Agent, or Firm* — Barclay Damon LLP; Anthony P. Gangemi (57) ABSTRACT

A simultaneous emission-transmission tomography in an MRI hardware framework is described. A method of multimodality imaging includes reconstructing, by a simultaneous emission transmission (SET) circuitry, a concentration image based, at least in part, on a plurality of selected γ-rays; and reconstructing, by the SET circuitry, an attenuation image based, at least in part, on the plurality of selected γ-rays. The plurality of selected γ-rays is emitted by a polarized radio tracer included in a test object. The selected (Continued)

γ-rays are selected based, at least in part, on a radio frequency (RF) pulse and based, at least in part, on a gradient magnetic field.

20 Claims, 8 Drawing Sheets (51) Int. Cl.
 A61B 6/03  (2006.01)
 A61B 6/42  (2024.01)
 G01R 33/038 (2006.01)
 G01R 33/38  (2006.01)

(52) U.S. Cl.
 CPC .......... *A61B 6/4417* (2013.01); *A61B 6/5235* (2013.01); *G01R 33/0385* (2013.01); *G01R 33/38* (2013.01)

(56) References Cited

U.S. PATENT DOCUMENTS

| | | |
|---|---|---|
| 2008/0073543 A1 | 3/2008 | Vija et al. |
| 2008/0219534 A1 | 9/2008 | Faul et al. |
| 2016/0084971 A1 | 3/2016 | Cates, Jr. et al. |
| 2016/0238684 A1 | 8/2016 | Steinbach et al. |
| 2016/0282432 A1 | 9/2016 | Wang |

OTHER PUBLICATIONS

Gjesteby, L., et al., "Simultaneous Emission-transmission Tomography (SET)," The 14th International Meeting on Fully Three-Dimensional Image Reconstruction in Radiology and Nuclear Medicine, pp. 363-371, Jun. 2017.

Kavitha, C.T., et al., "Medical image fusion based on hybrid intelligence," Applied Soft Computing, vol. 20, pp. 83-94, Jul. 2014.

Gjesteby, L., et al., "Numerical study on simultaneous emission and transmission tomography in the MRI framework," Proc. SPIE, vol. 10391, pp. 1-9, Sep. 19, 2017.

Pfluger, T., et al., "Multimodal Imaging Using PET and MRI," Pediatric PET Imaging, Chapter 27, pp. 485-501.

Yamauchi, Y., et al., "Novel attenuation correction of SPECT images using scatter photopeak window data for the detection of coronary artery disease," Journal of Nuclear Cardiology, vol. 21, No. 1, pp. 109-117, Jan. 2014.

SIMULTANEOUS EMISSION-TRANSMISSION TOMOGRAPHY IN AN MRI HARDWARE FRAMEWORK

CROSS REFERENCE TO RELATED APPLICATION(S)

This application claims the benefit of U.S. Provisional Application No. 62/642,645, filed Mar. 14, 2018, and U.S. Provisional Application No. 62/686,727, filed Jun. 19, 2018, which are both incorporated by reference as if disclosed herein in their entirety.

FIELD

The present disclosure relates to tomography, in particular to, simultaneous emission-transmission tomography (SET) in a magnetic resonance imaging (MRI) hardware framework.

BACKGROUND

Multi-modal/hybrid systems that combine imaging modalities have benefitted the medical imaging field. For example, positron emission tomography (PET) may be combined with either computed tomography (CT) or magnetic resonance imaging (MRI). PET-CT can provide functional information co-registered with structural images from CT. PET-MRI can deliver complementary functional and morphological information with relatively high-sensitivity and relatively rich soft tissue contrast. A synergy between nuclear and magnetic imaging techniques has enabled a number of advancements in diagnostics and therapy.

SUMMARY

In some embodiments, a method of multimodality imaging includes reconstructing, by a simultaneous emission transmission (SET) circuitry, a concentration image based, at least in part, on a plurality of selected γ-rays; and reconstructing, by the SET circuitry, an attenuation image based, at least in part, on the plurality of selected γ-rays. The plurality of selected g-rays is emitted by a polarized radio tracer included in a test object. The selected γ-rays are selected based, at least in part, on a radio frequency (RF) pulse and based, at least in part, on a gradient magnetic field.

Some embodiments of the method further include providing, by a main magnetic field source device, a uniform main magnetic field to the test object; adjusting, by a gradient magnetic field device, the main magnetic field to yield the gradient magnetic field; and providing, by RF source circuitry, the RF pulse to the test object.

In some embodiments of the method, the reconstructed images correspond to the entire test object. In some embodiments of the method, the reconstructed images correspond to a region of interest included in the test object.

In some embodiments of the method, the adjusting is configured to select γ-rays emitted from a location with pixel resolution. In some embodiments of the method, the adjusting is configured to select γ-rays emitted from a location with a fraction of a pixel resolution. In some embodiments of the method, the main magnetic field source device is stationary. In some embodiments of the method, the main magnetic field source device is configured to rotate about the test object. In some embodiments of the method, the reconstructing is based, at least in part, on a known tracer concentration at a reference point pixel.

In some embodiments, a simultaneous emission transmission (SET) system includes a SET circuitry. The SET circuitry is configured to reconstruct a concentration image based, at least in part, on a plurality of selected γ-rays and to reconstruct an attenuation image based, at least in part, on the plurality of selected γ-rays. The plurality of selected γ-rays is emitted by a polarized radio tracer included in a test object. The selected γ-rays are selected based, at least in part, on a radio frequency (RF) pulse and based, at least in part, on a gradient magnetic field.

Some embodiments of the system further include a main magnetic field source device, a gradient magnetic field device and an RF source circuitry. The main magnetic field source device is configured to provide a uniform main magnetic field to the test object. The gradient magnetic field device is configured to adjust the main magnetic field to yield the gradient magnetic field. The RF source circuitry is configured to provide the RF pulse to the test object.

In some embodiments of the system, the reconstructed images correspond to the entire test object. In some embodiments of the system, the reconstructed images correspond to a region of interest included in the test object.

In some embodiments of the system, the adjusting is configured to select γ-rays emitted from a location with pixel resolution. In some embodiments of the system, the adjusting is configured to select γ-rays emitted from a location with a fraction of a pixel resolution. In some embodiments of the system, the main magnetic field source device is stationary. In some embodiments of the system, the main magnetic field source device is configured to rotate about the test object. In some embodiments of the system, the reconstructing is based, at least in part, on a known tracer concentration at a reference point pixel.

In some embodiments, a device includes means for performing any embodiment of the method.

In some embodiments, a computer readable storage device has stored thereon instructions that when executed by one or more processors result in the following operations including any embodiment of the method.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

In one example, a system and method, called "polarized nuclear imaging" (PNI), are configured to perform nuclear imaging in an MRI hardware framework. The method is configured to provide a two-dimensional concentration image of a polarized radioactive tracer. The detection scheme is made possible by nuclear polarization and magnetic manipulation of a radio tracer and exploits the directional preference of gamma rays ("γ-rays") emitted from polarized nuclei. The polarized tracer creates anisotropic emission of γ-rays with a known and controllable directional preference. An MRI-type perturbation strategy for spatial encoding may be employed to collect the emitted γ-ray signals for tomographic reconstruction. Gradient magnetic fields and an RF pulse sequence "activate" a specific region of pixels or voxels so that γ-rays from only those regions are directed into the transverse direction for measurement by a detector pair. The principles of PNI provide: (1) better image resolution than that of classical nuclear imaging, (2) higher signal sensitivity than that of advanced MRI, and (3) closer and easier integration of three major imaging modalities (CT, SPECT (single photon emission computed tomography) and MRI).

The PNI technique does not provide attenuation background imaging.

Generally, the present disclosure relates to an acquisition process that improves upon the PNI technique by reconstructing both a concentration image and an attenuation image from a same γ-ray dataset. The method, apparatus and/or system is configured for multimodality imaging. The multimodality imaging corresponds to simultaneous emission-transmission tomography (SET). It is contemplated that the method, apparatus and/or system may be extended for MRI with the hardware framework in place. SET is both a structural and functional tomographic imaging technique that uses polarized radio tracers as a medium to probe cellular and molecular targets and measure the attenuation background at the same time. Simultaneous acquisition of emission and transmission data is configured to facilitate reconstruction of background attenuation and radio tracer concentration images (i.e., "attenuation image" and "concentration image"). This information can be used to pinpoint the location of cancerous tissue and reveal the molecular makeup. A half-voxel activation method is configured to reduce reconstruction errors and supports a unique solution to the inverse problem, as will be described in more detail below.

In MRI, initially a homogeneous background magnetic field is applied resulting in all the magnetization vectors (corresponding to spins, i.e., protons) associated with individual pixels/voxels, aligning along the direction of the background magnetic field. A pulse sequence is then applied to perturb these vectors and produce nonzero components on a plane perpendicular to the main field. These in-plane vectors generate alternating electromagnetic fields in nearby coils to produce so-called free induction decay (FID) signals. The recorded data are approximated as position-specific samples of the Fourier transform of the patient or animal to be tomographically reconstructed. The samples are known as k-space data.

Generally, the present disclosure relates to a multimodality method and a simultaneous emission transmission (SET) system configured to reconstruct, by a SET circuitry, a concentration image based, at least in part, on a plurality of selected γ-rays. The method and/or system further includes reconstructing, by the SET circuitry, an attenuation image based, at least in part, on the plurality of selected γ-rays. The plurality of selected g-rays is emitted from a polarized radio tracer included in a test object. The plurality of selected γ-rays are selected based, at least in part, on a radio frequency (RF) pulse and based, at least in part, on a gradient magnetic field.

Thus, the method and/or system are configured to acquire simultaneous emission and transmission data from γ-ray measurements of a polarized radionuclide (i.e., radio tracer) activated by MIll hardware and to provide a potential for magnetic resonance imaging in synchrony. The combined information, that is co-registered, may provide insight into morphological features and molecular activity in the test object and/or a region of interest (ROI) within the test object. A hybrid imaging system, that combines CT, nuclear imaging and MIll, may then provide registered morphological, functional and cellular/molecular information simultaneously and quantitatively, thus, facilitating precision medicine.

Generally, in operation, polarized (e.g., polarization greater than 60%) radioactive tracers may be injected into an object being imaged ("test object"). Polarization of the radio tracer can be achieved, for example, by a spin-exchange optical pumping technique, which uses infrared laser light to rearrange electrons. A main magnetic field, $B_0$, is configured to align the polarized radio tracer molecules along an axis of the magnetic field (z-direction). The main magnetic field may be created by Helmholtz coils. In one nonlimiting example, the magnetic field strength may be less than 0.1 T (Tesla). A first pair of γ-ray detectors may be positioned such that their respective detection surfaces oppose one another and are parallel to the longitudinal direction (z-direction) of the $B_0$ field. A second pair of γ-ray detectors may be positioned such that their detection surfaces oppose one another and are parallel to a transverse direction (x-direction or y-direction) relative to the main magnetic field. Each detector assembly may include a γ-ray detector and a respective collimator. The collimator grids on the detector are configured to allow only directly incident γ-rays to be measured.

Gradient coils may be configured to initially alter the $B_0$ field along the x-direction to create a $B_1$ gradient field. A radio frequency (RF) coil may then be configured to apply an RF pulse at a Larmor frequency configured to flip the polarized radio tracers to align in the transverse direction. The RF pulse is configured to select radio tracers located in a section of the $B_1$ field precessing at the specified Larmor frequency. Emitted γ-rays may then be detected perpendicularly by the longitudinal detectors, and the detected γ-rays are configured to be selected such that they may only be from the target region. This process can be repeated for multiple Larmor frequencies to detect signals from all regions of the radio tracer sample along one dimension. To image in a second dimension, gradient coils may then be configured to alter the $B_0$ field along the y-direction to create a second $B_1$ gradient field. The object may be translated in the z-direction to obtain full three-dimension reconstruction.

Figure 1:
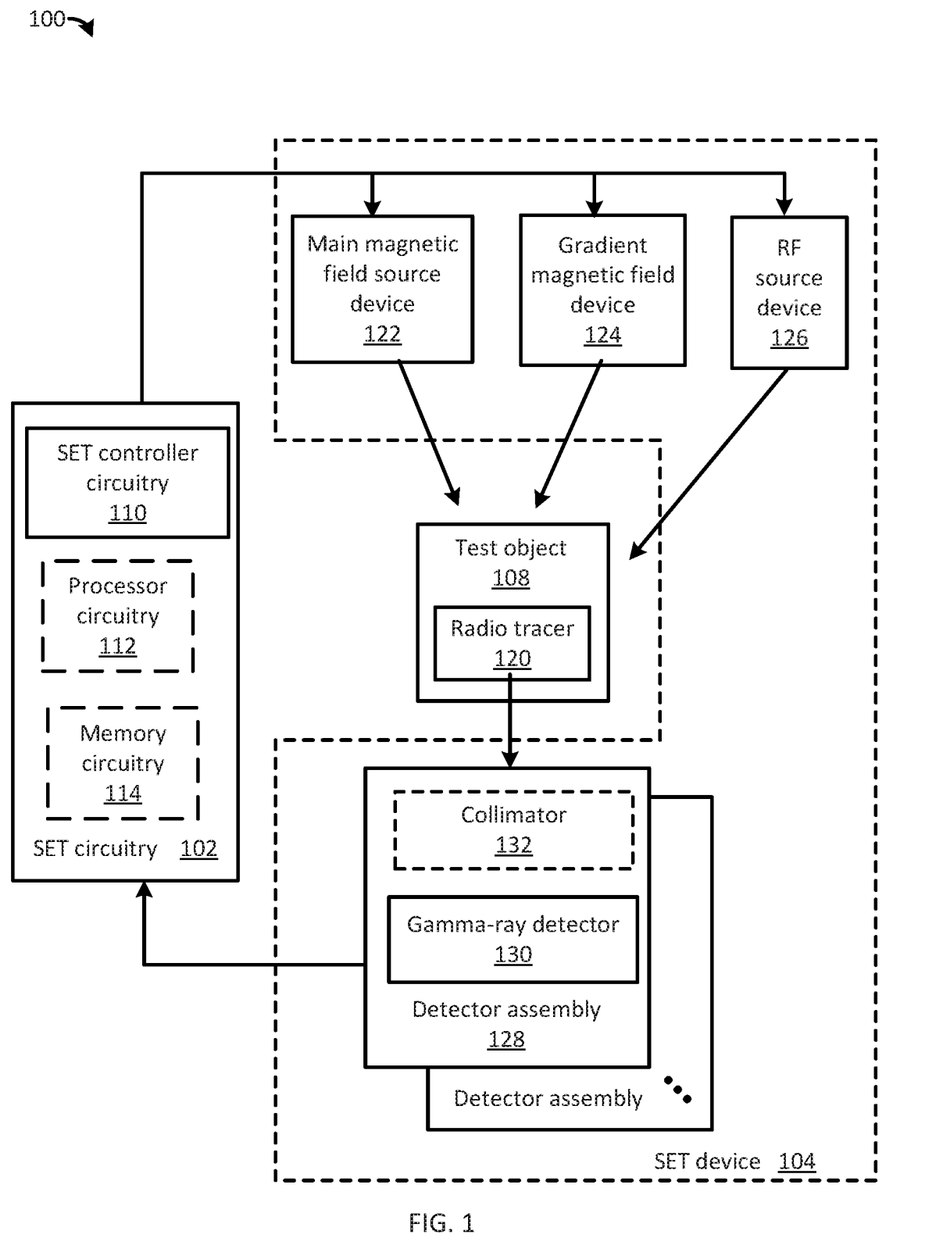
FIG. 1 illustrates a functional block diagram of a simultaneous emission-transmission tomography (SET) system consistent with several embodiments of the present disclosure.

FIG. 1 illustrates a functional block diagram 100 of a SET system consistent with several embodiments of the present disclosure. SET system 100 includes a SET circuitry 102 and a SET device 104. SET system 100 further includes a test object 108 that contains a radio tracer 120. The radio tracer 120 may be polarized, as described herein. SET circuitry 102 includes SET controller circuitry 110 and may include processor circuitry 112 and/or memory circuitry 114. SET device 104 includes a main magnetic field source device 122, a gradient magnetic field device 124, a radio frequency (RF) source device 126 and at least one detector assembly, e.g., detector assembly 128. The detector assembly 128 includes a gamma ray detector 130. In some embodiments, the detector assembly 128 may include collimator 132.

SET circuitry 102, e.g., SET controller circuitry 110, is configured to manage operation of SET system 100. SET controller circuitry 110 is configured to control operation of main magnetic field source device 122, gradient magnetic field device 124 and RF source device 126. Main magnetic field source device 122 is configured to produce, i.e., generate, a uniform magnetic field. The test object 108 is configured to be positioned within SET device 104 at a location within the uniform magnetic field. Gradient magnetic field device 124 is configured to adjust the main magnetic field to yield a gradient magnetic field. At least a portion of the test object 108 is configured to be positioned within the gradient magnetic field. RF source device 126 is configured to provide, i.e., generate and transmit, an RF pulse to the test object 108. Gamma ray detector 130 is configured to detect selected γ-rays emitted from radio tracer 120. The selected γ-rays may be emitted in response to the RF pulse. The output from detector assembly 128 is configured to correspond to a plurality of selected g-rays. The plurality of selected γ-rays may be selected based, at least in part, on the RF pulse(s) and based, at least in part, on the gradient magnetic field.

SET controller circuitry 110 is configured to receive output from detector assembly 128 and to determine (i.e., reconstruct) a concentration image and an attenuation image based, at least in part, on the output from detector assembly 128. In an embodiment, the images may correspond to the test object 108. In another embodiment, the images may correspond to a region of interest (ROI) within test object 108. As used herein, SET operations directed to an ROI within a test object are termed "interior" SET operations.

Figure 2:
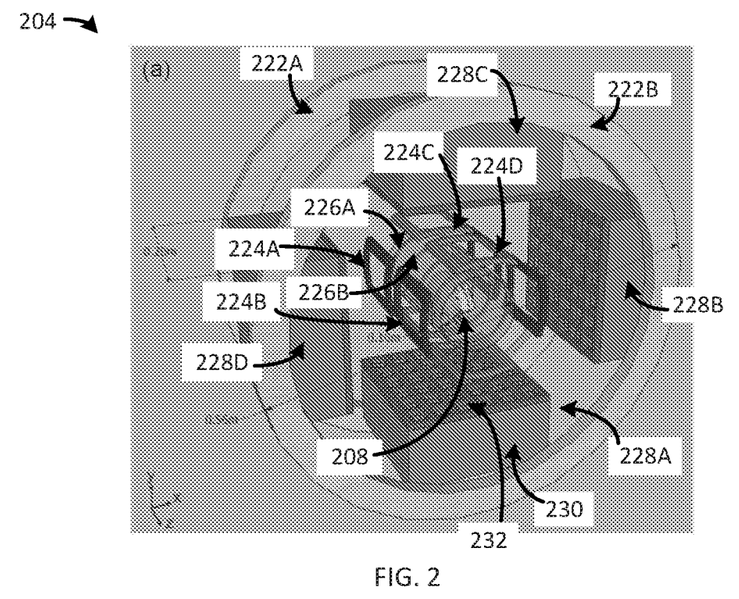
FIG. 2 is a sketch of one example SET device consistent with one embodiment of the present disclosure.

FIG. 2 is a sketch of one example SET device 204 consistent with one embodiment of the present disclosure. FIG. 2 further includes a test object 208. SET device 204 includes a plurality of Helmholtz coils 222A, 222B, a plurality (e.g., eight) of gradient coils, e.g., gradient coils 224A, ..., 224D, a plurality (e.g., four) of RF coils, e.g., RF coils 226A, 226B and a plurality of detector assemblies 228A, ..., 228D. The plurality of detector assemblies are oriented as two opposing pairs (e.g., 228A and 228C, 228B and 228D) with adjacent detector assemblies (e.g., 228A and 228B) oriented at an angle of 90 degrees to each other. Each detector assembly, e.g., detector assembly 228A, includes a γ-ray detector 230 and a collimator 232.

The Helmholtz coils 222A, 222B correspond to one example of the main magnetic field source device 122 of FIG. 1. The Helmholtz coils 222A, 222B are configured to be stationary, in this example. The plurality of gradient coils are one example of the gradient magnetic field device 124. The plurality of RF coils are one example of the RF source device 126. The plurality of detector assemblies 228A, ..., 228D are examples of detector assembly 128. The γ-ray detector 230 is one example of gamma-ray detector 130 and the collimator 232 is one example of collimator 132. In one nonlimiting example, the γ-ray detector 230 may correspond to a scintillator layer.

Figure 3:
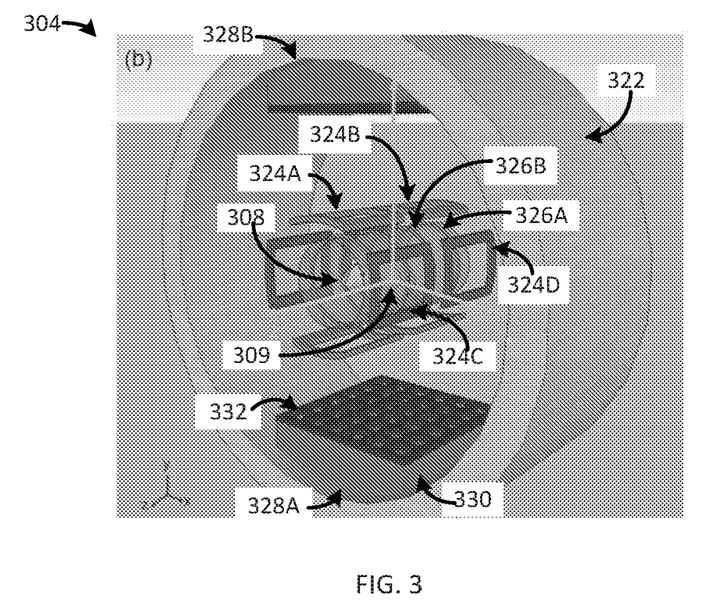
FIG. 3 is a sketch of another example SET device consistent with one embodiment of the present disclosure.

FIG. 3 is a sketch of another example SET device 304 consistent with one embodiment of the present disclosure. FIG. 3 further includes a test object 308 and an indication of a region of interest 309 included in the test object 308. FIG. 3 includes a set of three dimensional axes whose origin corresponds to the region of interest 309.

SET device 304 includes a Helmholtz coil assembly 322, a plurality (e.g., eight) of gradient coils, e.g., gradient coils 324A, ..., 324D, a plurality (e.g., four) of RF coils, e.g., RF coils 326A, 326B and a plurality of detector assemblies 328A, 328B. The detector assemblies 328A, 328B are oriented as an opposing pair. Each detector assembly, e.g., detector assembly 328A, includes a γ-ray detector 330 and a collimator 332. The Helmholtz coil assembly 322 is one example of the main magnetic field source device 122 of FIG. 1. The Helmholtz coil assembly 322 may be configured to rotate in this example. The plurality of gradient coils are examples of the gradient magnetic field device 124. The plurality of RF coils are examples of the RF source device 126. The plurality of detector assemblies 328A, 328B are examples of detector assembly 128. The γ-ray detector 330 is one example of gamma-ray detector 130 and the collimator 332 is one example of collimator 132.

Figures 4, 5, 6A, 6B:
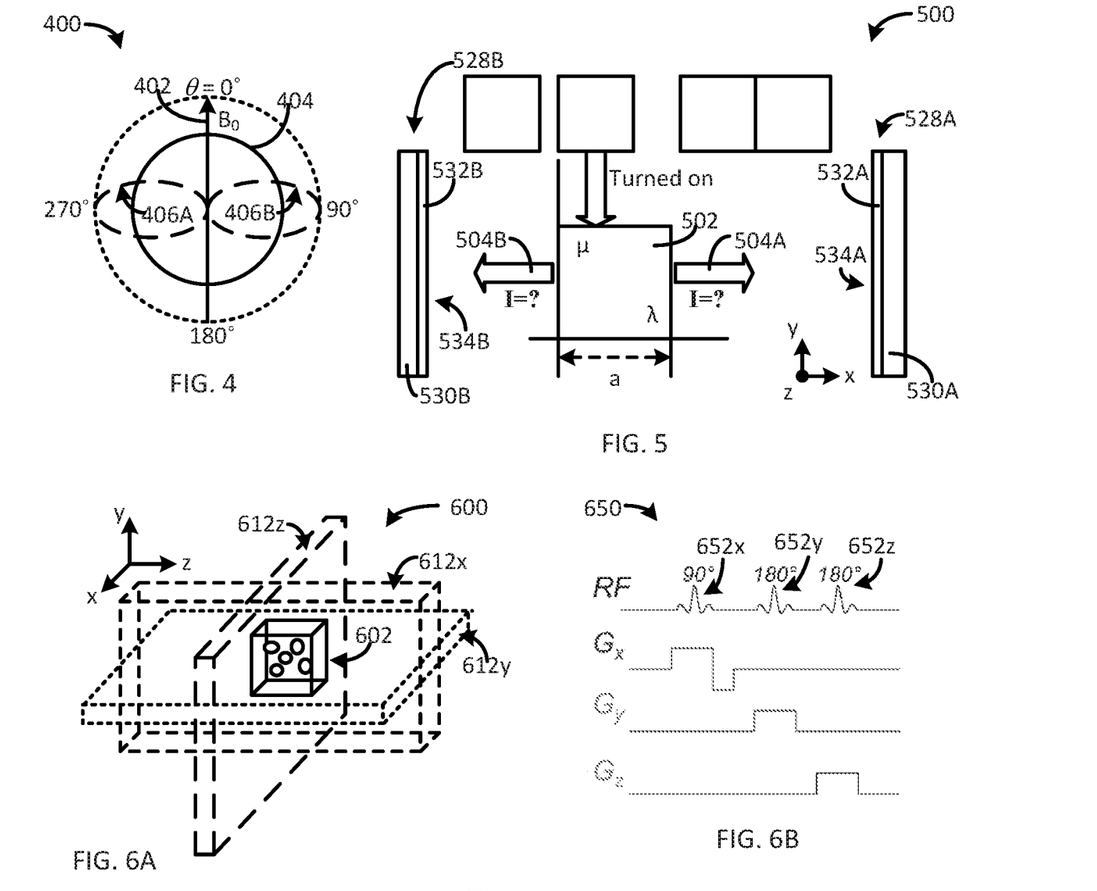
FIG. 4 illustrates one example of a simplified polar plot of the angular emission probability at varying levels of nuclei polarization of a radio tracer.
FIG. 5 is a sketch illustrating one example of selection of a pixel (and/or a voxel) for detecting emission of γ-rays.
FIGS. 6A and 6B are a sketch illustrating a selected voxel and a corresponding RF pulse sequence, respectively, for activating the selected voxel (and/or ROI)

FIG. 4 illustrates one example of a simplified polar plot 400 of the angular emission probability at varying levels of nuclei polarization of a radio tracer. An arrow 402 indicates a direction of the main magnetic field, $B_0$, and a nuclei orientation of a radio tracer, e.g., radio tracer 120 of FIG. 1. In other words, the nuclei orientation of the radio tracer is generally aligned with the direction of the main magnetic field. A first probability, represented by a solid circle 404, corresponds to angular emission direction probability without nuclei polarization. In other words, without nuclei polarization, angular emission direction probability is generally uniform for any direction. A second probability, represented by dotted ellipses 406A, 406B, corresponds to emission direction probability as polarization approaches 100%. The second emission probability 406A, 406B favors an axis perpendicular to the nuclei orientation, resulting in high count rates in a transverse detector.

Turning now to FIG. 1, SET system 100 is configured to utilize polarized radioactive tracers, e.g., radio tracer 120, as the source for tomographic imaging in a main magnetic field $B_0$. Nuclear spins of the radio tracer 120 may be substantially polarized. As used herein, "substantially polarized" means nuclear polarization of at least 60% in the perpendicular axis. In one nonlimiting example, the radio tracer 120 may be polarized up to a majority percentage, between 60-90%. Radio tracer 120 may include tracers with a nuclei spin number of greater than one half. Thus, radio tracer 120 may include, but is not limited to, isotopes $^{127m}Xe$, $^{131m}Xe$, $^{79m}Kr$, $^{132m}I$ and $^{81m}Rb$.

In one nonlimiting example, the radio tracer 120 may be polarized using a spin-exchange optical pumping technique to rearrange electrons with an infrared laser. The spin-exchange optical pumping method may be particularly suited to polarize noble gases. In another nonlimiting example, a hyperpolarization technique may be utilized to polarize condensed state molecules. For example, dynamic nuclear polarization can be utilized to polarize frozen solutes followed by rapid dissolution at room temperature. The anti-parallel spin-order in para-hydrogen (with ~99% purity) is able to hyperpolarize nuclei magnetization through double-bond addition reaction. When $H_2$ is frozen to solids, its constituting hydrogen atoms tend to have anti-parallel nuclear spins, due to the lower rotational energy of this spin isomer. After para-hydrogen is thawed, this spin order can be maintained for hours at room temperature, which is long enough for vascular delivery inside the body. Once the para-hydrogen reacts with a molecule containing an asymmetric double bond, the spin order of para-hydrogen can be transformed into hyperpolarized hydrogen in the reaction product. Para-hydrogen can also achieve Signal Amplification by Reversible Exchange (SABRE) in situ, via transient interaction with the test molecule through a metallic coordination center.

In an embodiment, the radio tracer distribution (i.e., a concentration image) and the attenuation background (i.e., attenuation image) may be reconstructed quantitatively and simultaneously from the same dataset (i.e., γ-ray measurements) that includes a plurality of selected γ-rays. A pair of gamma ray detectors may be configured to detect γ-rays along paths defined by corresponding collimators. The attenuation background may be compensated to facilitate performing quantitative SPECT imaging. The attenuation background may be utilized for the same purpose of CT scanning.

The distributions of emission intensities and attenuation coefficients can be decoupled mathematically. γ-rays from radioactive molecules at position r may be detected by a pair of opposing gamma ray detectors positioned on the left and right, $m_l(r)$ and $m_r(r)$, respectively, as:

$$m_l(r) = \Phi(r)\exp(-\int_\infty^r \mu(r')dr')$$

$$m_r(r) = \Phi(r)\exp(-\int_r^\infty \mu(r')dr') \quad (1)$$

where $\Phi(r)$ is the intensity of γ-rays at position r directly proportional to the concentration $\lambda(r)$ of a radioactive tracer and $\mu(r)$ is the corresponding linear attenuation coefficient. It should be noted that, as used herein, "left" and "right" are terms of convenience configured to identify, and indicate relative positions of, the opposing gamma ray detectors. If $\Phi(r) > 0$, and the measured intensity of γ-rays has a sufficient SNR (signal to noise ratio), the dual integral equations in Eq. (1) can be converted to:

$$\sqrt{m_l(r)m_r(r)} = \Phi(r)\exp(-\tfrac{1}{2}\int_{-\infty}^\infty \mu(r')dr') \quad (2)$$

Eq. (2) may then be rearranged to obtain a formula with respect to γ-ray emission intensity $\Phi(r)$ as:

$$\Phi(r) = \sqrt{m_l(r)m_r(r)}\exp(\tfrac{1}{2}\int_{-\infty}^\infty \mu(r')dr') \quad (3)$$

From Eq. (1-2), a formula with respect to attenuation coefficient $\mu(r)$ may be obtained as:

$$m_l(r) = m_r(r)\exp(\int_r^\infty \mu(r')dr' - \int_{-\infty}^r \mu(r')dr')$$

$$m_r(r) = m_l(r)\exp(\int_{-\infty}^r \mu(r')dr' - \int_r^\infty \mu(r')dr') \quad (4)$$

Once the attenuation background is known, the tracer concentration can be readily estimated from Eq. (3). Then, Eq. (4) can be discretized into a linear equation. In one nonlimiting example, the discretized linear equation may be solved using an inverse method. In another nonlimiting example, the discretized linear equation may be solved using a compressive sensing-based image reconstruction. The compressive sensing (CS) technique can achieve a relatively high quality result from fewer measurements than what the Nyquist sampling criterion indicates.

In operation, the polarized radioactive tracers may be injected into a test object. Nuclei of the polarized radio tracers may be configured to align along an axis (e.g., z-direction) of the main magnetic field, $B_0$. In one nonlimiting example, the main magnetic field may be provided by Hemholtz coils. Once the nuclei are polarized along the direction of the main magnetic field, a π/2 RF pulse at the Larmor frequency can tilt the polarization axes of nuclei along a transverse direction within a selected section of the main magnetic field. The selected section may include the test object and/or may correspond to a region of interest within the test object. $B_1$ gradient fields provided by gradient coils can alter the $B_0$ field along the y-direction (or x-direction) to perform spatial encoding by activating a line of pixels parallel to the x-direction (or y-direction) in the selected plane. Then, gamma ray detectors in the selected plane can measure γ-rays along the lines perpendicular to the y-direction (or the x-direction) in the plane through regions where significant signals are emitted.

FIG. 5 is a sketch 500 illustrating one example of selection of a pixel 502 (and/or a voxel) for detecting emission of γ-rays. As used herein, "pixel" or "voxel" corresponds to a target region (i.e., spatial location) of a test object and/or region of interest that may emit and attenuate γ-rays. Selection of the pixel corresponds to magnetically turning the pixel on (by, for example, providing a gradient magnetic field) and triggering emission by providing an RF pulse at an appropriate Larmor frequency. γ-rays 504A, 504B may then be simultaneously emitted and attenuated by the selected pixel 502 (and/or voxel). The selected γ-rays may then be detected by a pair of opposing detectors 530A, 530B. Each detector 530A, 530B may be included in a respective detector assembly 528A, 528B that also includes a respective collimator 532A, 532B.

A respective detection surface 534A, 534B of each detector 530A, 530B may be positioned parallel to a y-axis to measure photons emitted from voxels. Any section can be scanned in this way, since the transverse and longitudinal directions are user-defined. The selection of a section, a line in the section and/or a pixel in the line can be specifically activated using an appropriate RF pulse sequence.

FIGS. 6A and 6B are a sketch 600 illustrating a selected voxel 602 and a corresponding RF pulse sequence 650, respectively, for activating the selected voxel (and/or ROI). FIGS. 6A and 6B may be best understood when considered together. Three RF pulses 652x, 652y, 652z combined with gradients $G_x$, $G_y$ and $G_z$ in the x-, y-, and z-directions, respectively, can be used to activate any cross section (e.g., cross sections 612x, 612y, 612z), any line in the active section and/or any single voxel, e.g., voxel 602, along the line. The pulse sequence targeting a single voxel or a region of interest is known as "point-resolved spectroscopy". Nuclei within the intersection region 602 of the gradient pulses may undergo refocusing, and thus these selected nuclei may emit γ-rays along the line of detection. If a section (or a line in the section) is to be activated, one (or two) gradient(s) should be applied, and should be timed differently to facilitate focusing.

If a particular voxel or an ROI is to be activated, the x-, y-, and z-gradients Gx, Gy, Gz, may be used. Thus, nuclei within the active (i.e., selected) voxel 602 may be configured to emit γ-rays within a preferred planar slab towards a collimated detector pair. For more efficient data acquisition, the whole field of view can be modulated by sinusoidal or other basis functions, which is similar to k-space imaging for MRI but with an attenuation background.

Turning now to FIG. 1, the data acquisition process can be performed with mechanical collimator grids (e.g., collimator 132) or without them, as in a full-body SET system. With metallic collimators, the imaging process is easier to visualize and analyze. If no metallic collimators are used, the radioactive tracers may be flipped into more orientations to unravel projective entanglements in raw data. In principle, the PNI model can be enabled through magnetic flipping of polarized tracers. This is essentially a magnetic collimation scheme, in addition to the known mechanical collimation (for CT and SPECT), electronic collimation (for PET) and temporal collimation (optical imaging with early photons) schemes.

In some situations, a solution to pixel-/voxel-oriented activation may not be unique if the attenuating effect within a pixel/voxel cannot be ignored. In the case of a single pixel there are two independent unknowns (attenuation and concentration) and two dependent measurements (the flux from both sides is the same). This problem can be addressed by activating not only pixels/voxels individually but also mixed/halved pixels/voxels, creating new independent measurements. With the half-pixel/voxel offset activation, data become sufficient for the unique solution.

Figure 7:
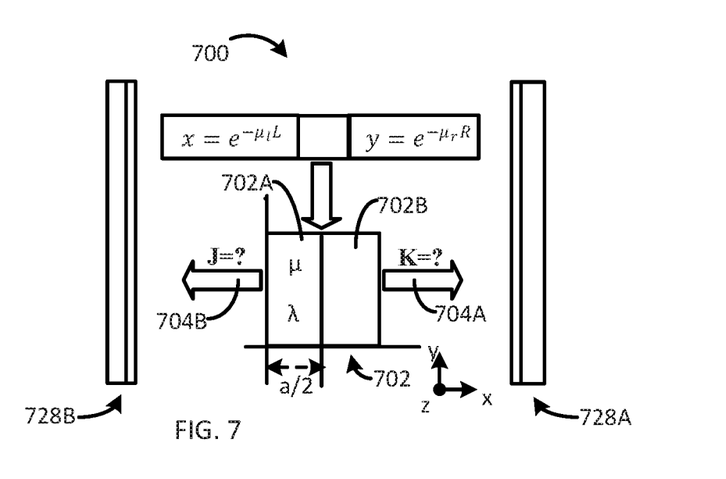
FIG. 7 is a sketch illustrating half-voxel offset activation.

FIG. 7 is a sketch 700 illustrating half-voxel offset activation. In a single voxel case, γ-ray signals 704A, 704B measured by a left collimated detector 728B and a right collimated detector 728A may be different when each half 702A, 702B of the voxel 702 is activated separately. Half-voxel activation for interior tomography is configured to enable a concentration image to be reconstructed without injecting a known radio tracer at a point. A line integral of attenuation coefficients along the line of active emission may be externally measured with a method such as radiography. The source concentration may then be determined based, at least in part, on the line integral. For example, the natural logarithm of the product of measurements from a detector pair may be proportional to the line integral of attenuation coefficients.

If external measurement is not available, it would still be helpful to computationally estimate the line integral based on an elastically deformed CT atlas. This process can be iteratively performed, and regularized with the reconstructed attenuation map of the ROI and other prior knowledge.

In some situations, Φ(r) (the intensity of γ-rays at position r) may satisfy Φ(r)>0 within one or multiple ROIs well inside the patient body, rather than for a entire field of view. A discrete model can be formulated for the active half of a given pixel/voxel, a/2, shown in FIG. 7. Then, the intensity measurements at each detector from the active side of the pixel/voxel can be expressed as follows:

$$J = \int_0^{\frac{a}{2}} \lambda \exp(-\mu(a-r)) dr \quad (5)$$

$$= \frac{\mu}{\lambda}\left(1 - \exp\left(-\frac{\mu a}{2}\right)\right)$$

$$K = \exp\left(-\frac{\mu a}{2}\right) * J \quad (6)$$

where J corresponds to γ-ray signal 704B and K corresponds to γ-ray signal 704A. The measurements J and K will be different when each half 702B, 702A of the voxel 702 is activated due to different paths of attenuation. The four measurements can be represented by the following:

$$m_{J_1} = \frac{a\lambda}{2} x \quad (7)$$

$$m_{K_1} = \frac{a\lambda}{2}\left(1 - \frac{a\mu}{2}\right) y \quad (8)$$

$$m_{J_2} = \frac{a\lambda}{2}\left(1 - \frac{a\mu}{2}\right) x \quad (9)$$

$$m_{K_2} = \frac{a\lambda}{2} y \quad (10)$$

The outside attenuation effects, x and y, can be divided out by taking a ratio of consecutive half-voxel measurements in a detector. This allows an expression for attenuation of the active pixel to be written as:

$$\frac{m_{J_2}}{m_{J_1}} = \left(1 - \frac{a\mu}{2}\right) \quad (11)$$

$$\mu = 2\left(\frac{1}{a} - \frac{m_{J_2}}{a m_{j_1}}\right)$$

An equation to determine the concentration at a given pixel may be expressed as:

$$\ln(m_{J_1} m_{K_2}) - a\mu = 2\ln\left(\frac{a\lambda}{2}\right) - LineIntegral \quad (12)$$

where the LineIntegral can be determined by either global reconstruction of the attenuation background, or by radiography in the case of interior reconstruction. A further propagation/attenuation process towards a detector element may be modeled according to a discretized Beer-Lambert law. In this way, a system matrix A can be constructed to solve the Ax=b inverse problem.

Figure 8:
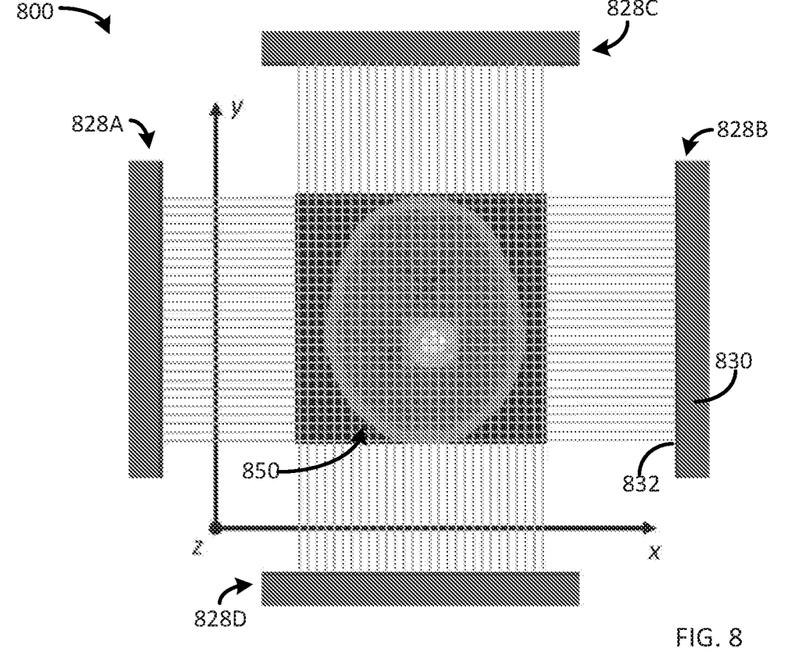
FIG. 8 illustrates imaging geometry showing detector position relative to a numerical phantom during measurements of emitted γ-rays.

FIG. 8 illustrates imaging geometry 800 showing detector position relative to a numerical phantom 850 during measurements of emitted γ-rays. Imaging geometry 800 includes two detector assembly pairs 828A and 828B and 828C and 828D. Each detector assembly, e.g., detector assembly 828B, includes a detector 830 and a collimator 832. A first pair includes opposing detector assemblies 828A and 828B and a second pair includes opposing detector assemblies 828C and 828D. The first pair 828A, 828B is perpendicular to the second pair 828C, 828D.

Operations configured to reconstruct attenuation coefficients, for each half of the pixel (row, column) and assuming that each measured intensity is nonzero, may include:
  setting a component of vector b, corresponding to the active half-pixel to a logarithmic ratio of measurements from the first and second detector (Eqs. (7) through (10)); and
  constructing the corresponding rows and columns of system matrix A. The coefficients contained in A depend on pixel positions relative to the active half-pixel (each of which is configured to determine a contribution of a selected attenuating pixel to the normalized measurement).

Operations may further include solving the inverse problem to recover attenuation coefficients. It may be appreciated that the solution will be unique if the pixel is sufficiently small.

Operations configured to recover a radio tracer concentration distribution, for each pixel along a row direction, may include:

finding flux escaping each side of the pixel using the Beer-Lambert law in a reverse order in terms of the reconstructed attenuation coefficients and known intensity measurements from each detector;

computing an average of the two flux estimates; and solving for the concentration of the pixel (Eq. (12)).

Under ideal circumstances, the radio tracer may be relatively widely distributed in the subject being imaged with high SNR so that the tissue attenuation can be accurately reconstructed from γ-ray signals everywhere. In practical cases, where extensive perfusion of the tracer does not occur, a different reconstruction method may be warranted. In these cases, interior tomography may be formulated to reconstruct the attenuation coefficients in an ROI where the tracer concentration is significant, according to a continuous model. Then, to recover the tracer concentration within the ROI, effects of the object attenuation outside the tracer ROI may be estimated.

Figure 9:
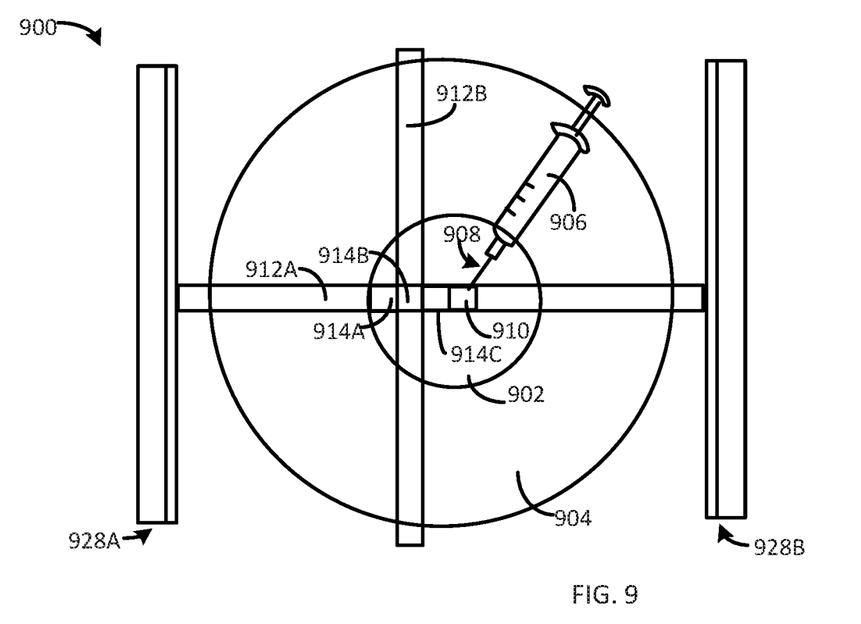
FIG. 9 is a sketch illustrating interior SET aided by a single measurement with a known source point.

FIG. 9 is a sketch 900 illustrating interior SET aided by a single measurement with a known source point 910. The sketch 900 includes a tracer ROI 902 and a remaining object region 904. A probe syringe 906 containing a known tracer concentration is coupled to a probe needle 908 that may be inserted into the tracer ROI 902. The known tracer is configured to establish a reference point pixel 910. The γ-ray intensities may then be measured by a collimated detector pair 928A, 928B.

Thus, a source point 910 may be introduced into the tracer ROI 902 by an injection containing a small volume of radio tracer with a known concentration. The detectors 928A, 928B may then be configured to measure the emitted γ-ray intensities along a line through the ROI 902. Attenuation effects may be determined on both sides of the entire path length using the Beer-Lambert Law.

The attenuated measurements may be configured to cover both the inner ROI 902 and path segments 912A, 912B that intersect at the active pixel 910. Since the attenuation coefficients in the tracer ROI 902 have already been determined, the attenuation of the non-tracer path section can be estimated from the difference. The tracer concentrations along the line inside the ROI 902 may then be recovered. Additional pixels, e.g., pixels 914A, 914B, 914C, in the ROI 902 may then be activated to determine attenuation effects of other segments 912A, 912B outside the ROI 902 to eventually recover the entire concentration distribution within the ROI 902.

Figure 10:
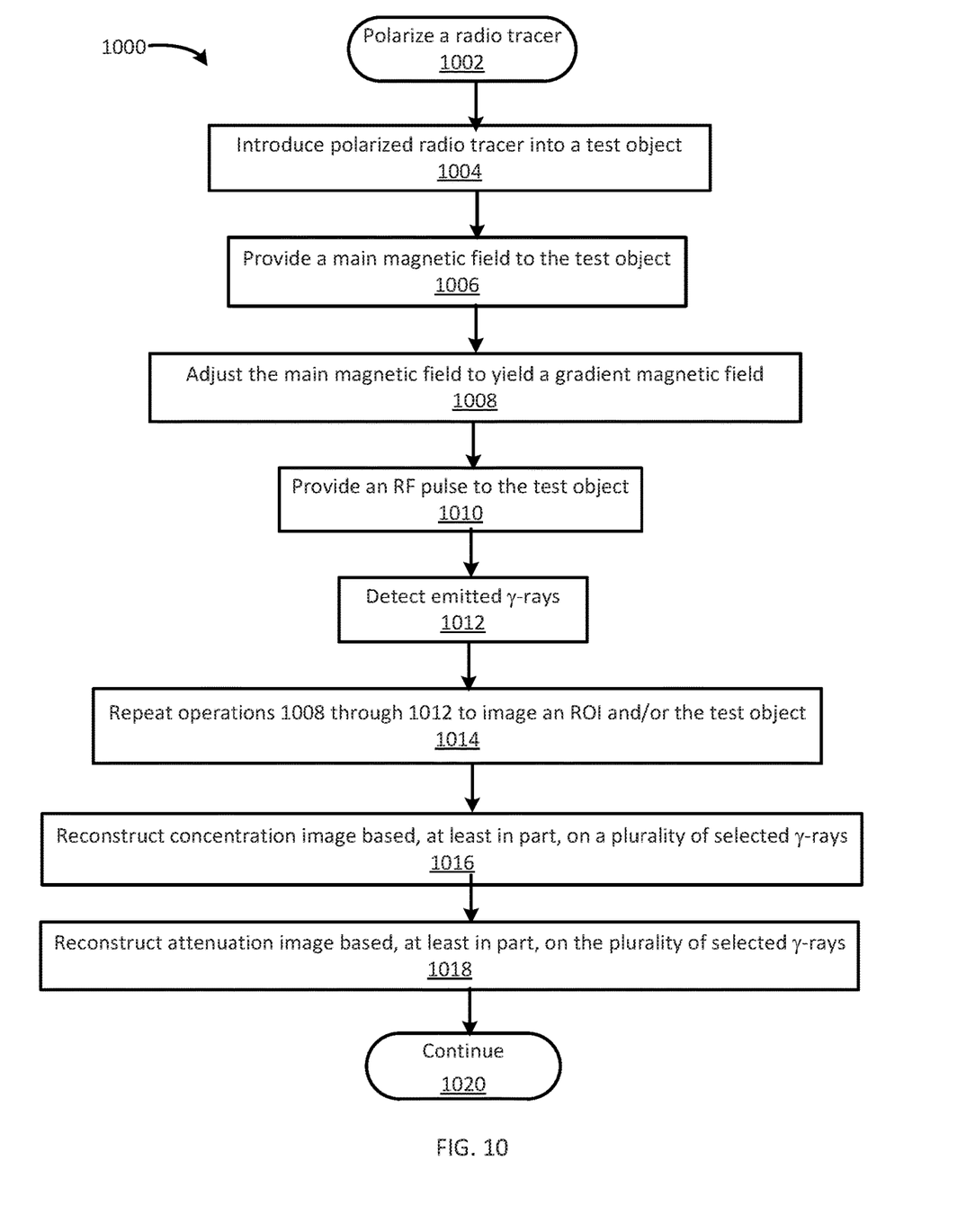
FIG. 10 is an example flowchart of multimodality imaging operations consistent with several embodiments of the present disclosure.

FIG. 10 is an example flowchart 1000 of multimodality imaging operations consistent with several embodiments of the present disclosure. In particular, flowchart 500 illustrates reconstructing a concentration image and reconstructing an attenuation image based, at least in part, on a plurality of selected γ-rays. The operations of flowchart 1000 may be performed by, for example, SET circuitry 102 (e.g., SET controller circuitry 110) and/or SET device 104 of FIG. 1.

Operations of flowchart 1000 may begin with polarizing a radio tracer at operation 1002. The polarized radio tracer may be introduced into a test object at operation 1004. In one nonlimiting example, the polarized radio tracer may be inserted into the test object. In another example, the polarized radio tracer may be injected into the test object. A main magnetic field may be provided to the test object at operation 1006. The main magnetic field may be adjusted to yield a gradient magnetic field at operation 1008. An RF pulse may be provided to the test object at operation 1010. Emitted γ-rays may be detected at operation 1012.

Operations 1008 through 1012 may be repeated at operation 1014 to image an ROI and/or the test object. A concentration image may be reconstructed based, at least in part, on a plurality of selected γ-rays at operation 1016. The plurality of selected γ-rays may be selected based, at least in part, on the RF pulse and based, at least in part, on the gradient magnetic field. An attenuation image may be reconstructed based, at least in part, on the plurality of selected γ-rays at operation 1018. Program flow may then continue at operation 1020.

Thus, a concentration image and an attenuation image may be reconstructed based, at least in part, on a plurality of selected γ-rays.

EXAMPLES

In the examples, two dimensional (2D) mechanical collimator grids with 0.5 mm$^2$ holes and a relatively thin wall of γ-ray blocking material between each hole were assumed. It may be appreciated that collimators are used at the cost of a compromised detection efficiency. A most efficient utilization of emitted γ-rays will be achieved in a whole body SET configuration that assumes a full detection coverage of the patient without mechanical collimation.

The γ-ray intensity measurements were simulated based on the discretized forward model of Eqs. (5-6). The simulation was not tailored to a specific radionuclide or decay time. The pixel size was set to 0.5 mm. An image matrix was 128×128 pixels. From $m_l$ and $m_r$ measurements of each active half-pixel, the attenuation and concentration images were reconstructed. A brain phantom was generated from a brain CT image (courtesy of Dr. Frank Gaillard, Radiopaedia.org) to demonstrate SET numerically according to Eqs. (5-12). The half-voxel activation technique was simulated for two different phantom cases.

The first case assumed that a radio tracer was distributed in the whole phantom with a background concentration of 0.05 MBq/ml, and that it became more significantly concentrated in ROIs. Specifically, eight ROIs were defined with concentrations ranging from 0.150 to 0.325 MBq/ml. The second case assumed that radio tracer was isolated to one ROI and was not widely distributed outside. When radio tracers were limited to ROIs, the interior SET method was used to calculate the attenuation coefficients in the tracer regions. Then, the remaining background attenuation effects were found by one of two ways. First, the method of probing the phantom with a tracer point source of known concentration was demonstrated as described herein with respect to FIG. 9. Second, it was shown that a known tracer injection may not be necessary if the line integrals along one dimensional can be determined as prior knowledge. This can be achieved by a simple radiograph.

Figure 11:
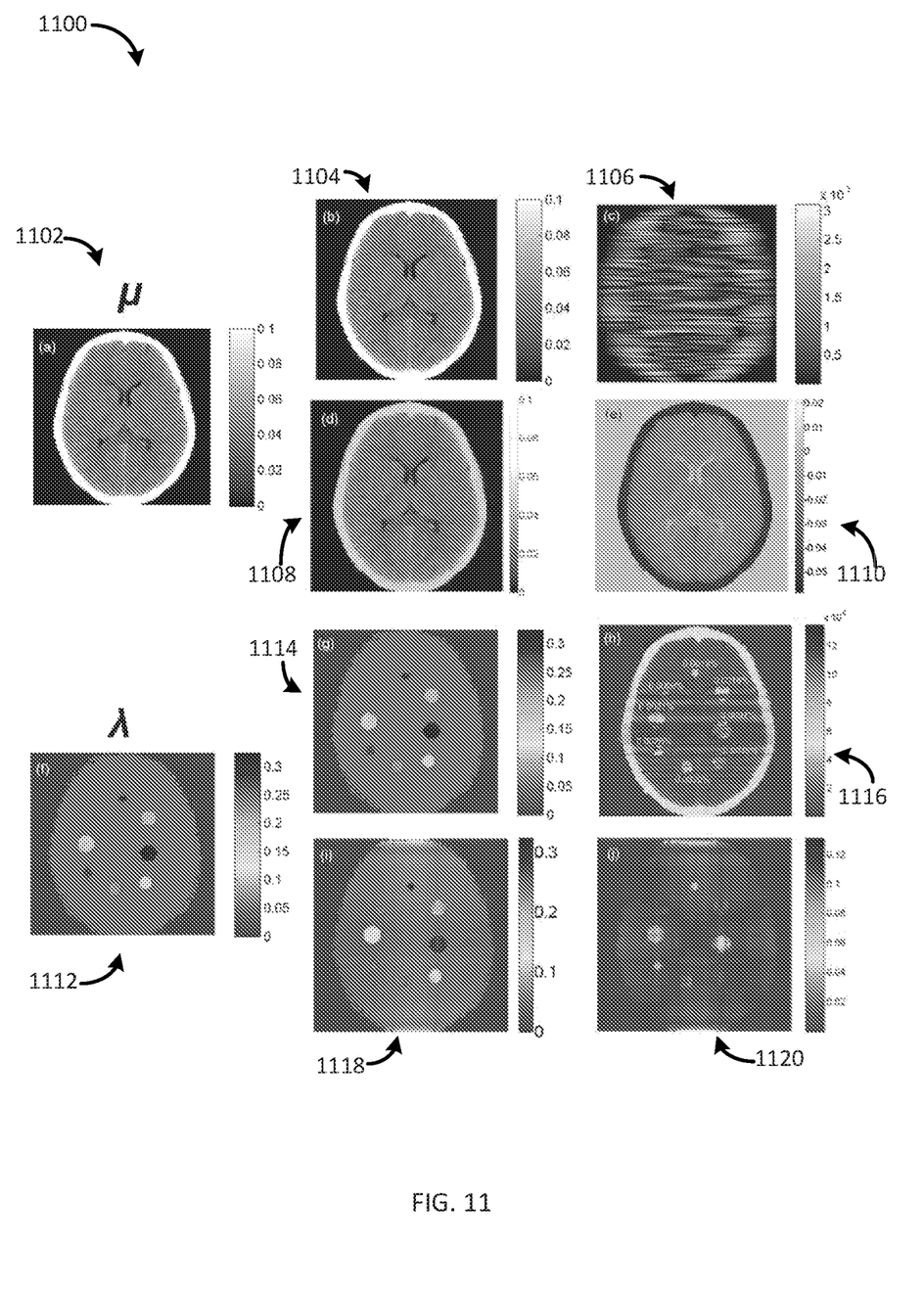
FIG. 11 illustrates one example of SET reconstruction from half-voxel activation measured by detectors on each side of the head phantom.

FIG. 11 illustrates one example 1100 of SET reconstruction from half-voxel activation measured by detectors on each side of the head phantom. Example 1100 includes a ground truth attenuation image (cm$^{-1}$) 1102, a reconstruction result without noise 1104 and a difference 1106. Example 1100 further includes a reconstruction result with noise added 1108, and a difference compared to ground truth 1110. Example 1100 further includes a ground truth concentration image (MBq/ml) 1112, a reconstruction result without noise 1114, and the difference image with mean error percentages for each ROI shown 1116; a reconstructed radio tracer concentration image with noise added 1118 and the difference compared to the ground truth 1120.

Example 1100 illustrates the case of the phantom containing widely distributed tracer activities. The ground truth and noise-free reconstructed images of the attenuation are shown along with the corresponding difference image in images 1102, 1104, 1106, respectively. The mean reconstruction error of the attenuation map 1106 was 2.58% in the brain region, with the largest errors in attenuation coefficient occurring at the edges. Images 1112, 1114, 1116 illustrate the ground truth and noise-free reconstructed images of the radio tracer distribution along with the difference image, respectively. The concentration images calculated from the estimated attenuation values show good agreement with the ground truth, as the mean concentration errors in the ROIs range between 0.0007% and 0.0028%, as noted in image 1116.

A Poisson distribution of the measurements was then used to simulate noise when the photon counts were set to $10^8$. This estimate is based on the measurement of $5 \times 10^5$ photon counts per second of $^{131m}$Xe as reported by the PNI methods. Over a several minute acquisition, the total photons would be approximately $10^8$. Note that this is a conservative case. It is contemplated that, in the future, a higher emission efficiency could be expected of a polarizable tracer. Images 1108, 1110 illustrate the attenuation image reconstructed from simulated noisy data, along with the difference compared to ground truth. Images 1118, 1120 illustrate the noisy reconstruction of the radio tracer concentration image and the difference image. Noise increased the errors in both images.

Figure 12:
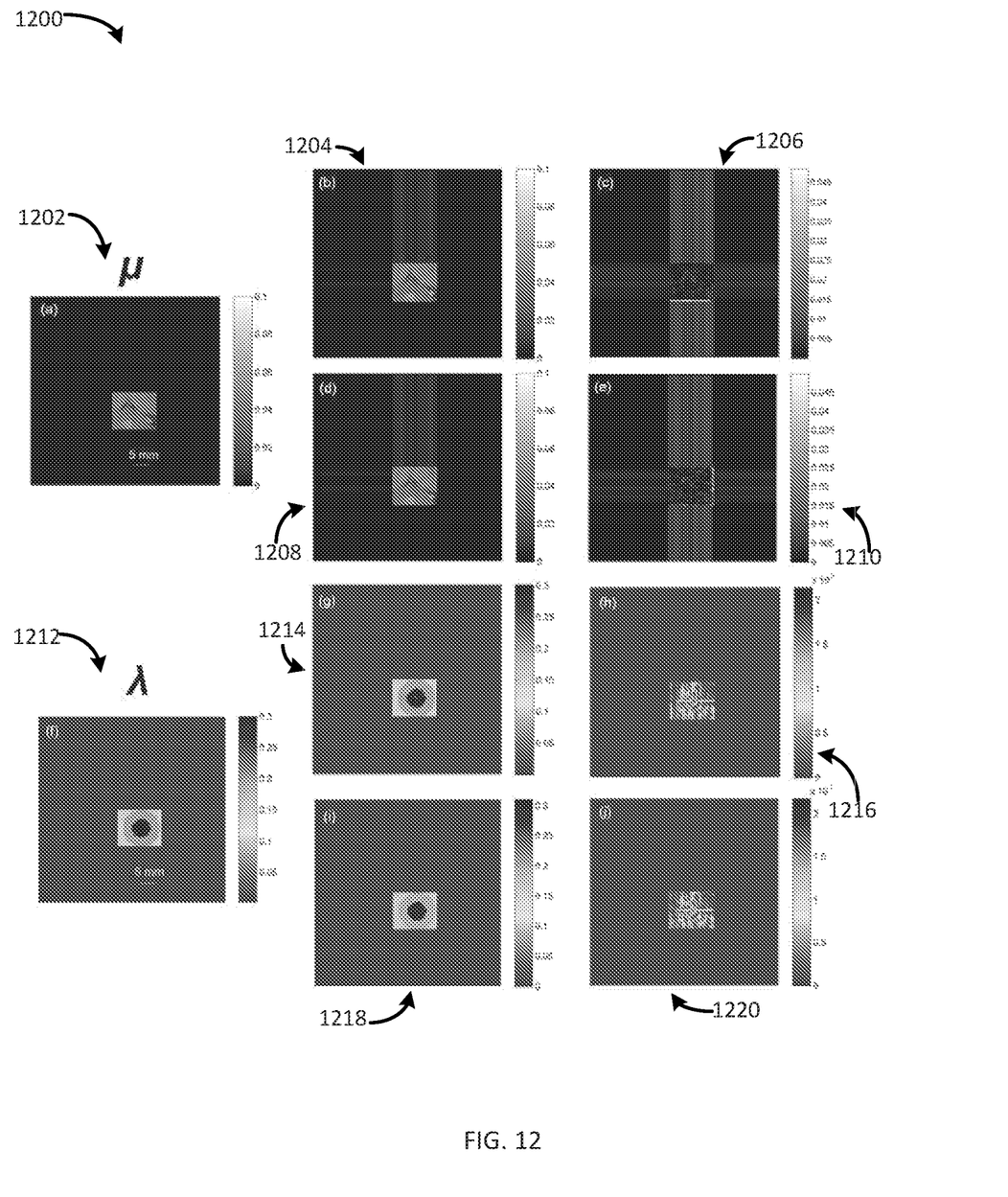
FIG. 12 illustrates one example of interior (i.e., ROI) SET reconstruction results measured by detectors on each side of the head phantom in the vertical and horizontal directions.

FIG. 12 illustrates one example 1200 of interior (i.e., ROI) SET reconstruction results measured by detectors on each side of the head phantom in the vertical and horizontal directions. A known source point of radio tracer was injected to facilitate determination of the concentration map. Example 1200 includes a ground truth ROI attenuation image (cm$^{-1}$) 1202, a reconstructed attenuation image without noise 1204 and a difference compared to ground truth 1206. Example 1200 further includes a reconstructed attenuation image with noise added 1208 and a difference compared to the ground truth 1210. Example 1200 further includes a ground truth ROI radio tracer concentration image (MBq/ml) 1212, a reconstructed concentration image without noise 1214 and a difference 1216. Example 1200 further includes a reconstructed radio tracer concentration image with noise 1218 and a difference compared to the ground truth 1220.

Example 1200 illustrates an interior SET technique noise-free and with Poisson noise added. Using the same brain phantom, a small region of radio tracer was defined slightly off-center. The ground truth attenuation and concentration maps corresponding to the ROI are shown in examples 1202 and 1212, respectively. Measurements were obtained from the ROI. Then, interior SET was used to reconstruct the attenuation coefficients and lumped effects inside and outside the ROI respectively.

Next, a known concentration of tracer was "injected" inside the ROI to allow estimation of attenuation effects outside the ROI along a line of emission. Using this information, the concentration was calculated for each pixel along the line. After this operation, all the concentration values along the lines intersecting the pixels with known concentrations inside the ROI can be considered known, without any additional need to introduce a known concentration point into the ROI. Using each solved "active" pixel along the same line as the known concentration point, the process can be repeated for other lines to recover the entire ROI radio tracer distribution. Examples 1204, 1206, 1214, 1216 illustrate the reconstructions and difference maps obtained using the interior SET method without noise. The mean error within the ROI of the attenuation image was 9.5% and the mean error in the concentration image was 0.38%. Examples 1208, 1210, 1218, 1220 illustrate the reconstructions and difference images with Poisson noise added. The mean error in the attenuation image was 11.3% and the mean error in the concentration image was 0.42%.

Figure 13:
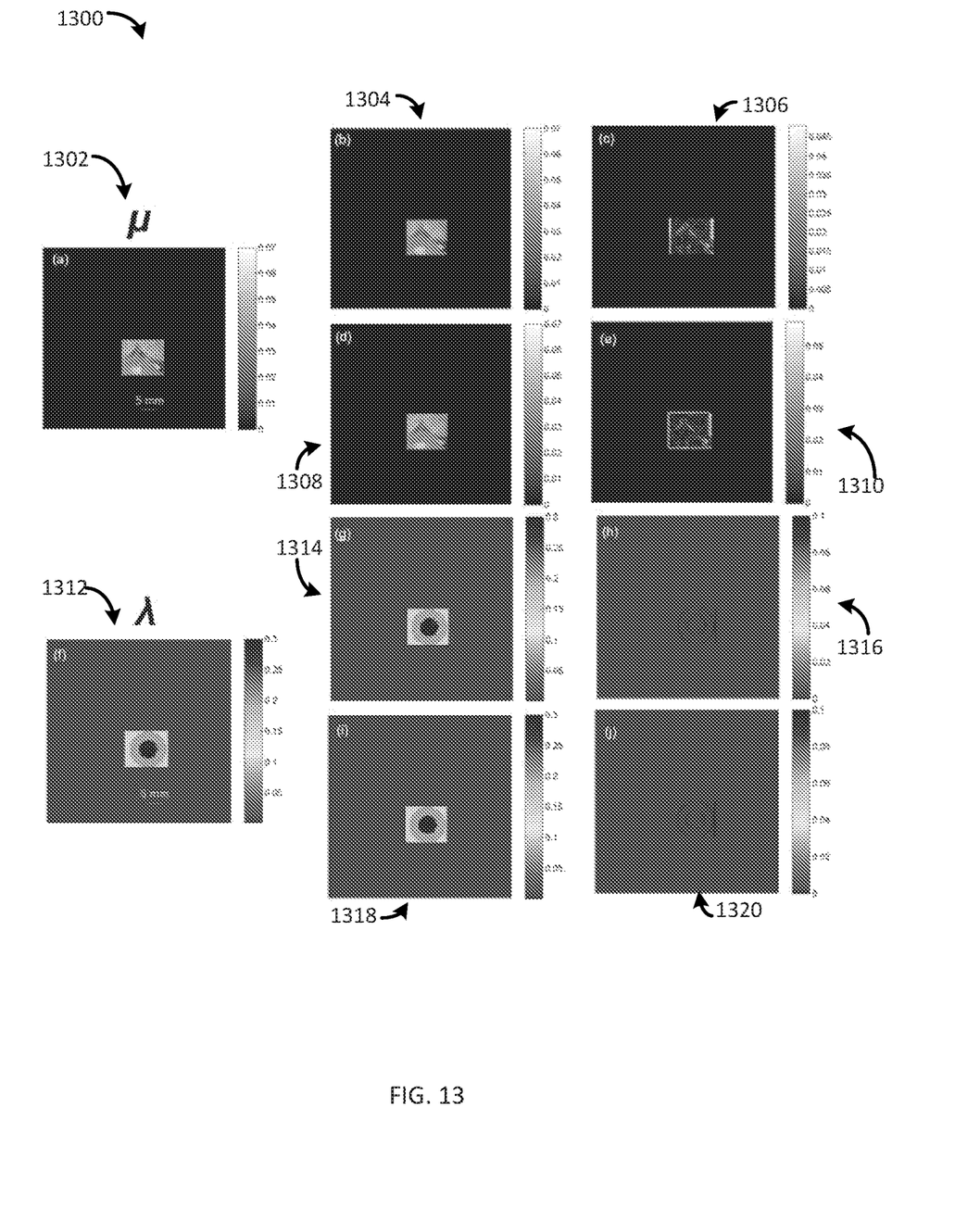
FIG. 13 illustrates one example of interior SET reconstruction results using the half-voxel activation scheme.

FIG. 13 illustrates one example 1300 of interior SET reconstruction results using the half-voxel activation scheme. Attenuation line integrals along the horizontal direction were assumed to be known outside the ROI to facilitate determination of the concentration map. Example 1300 includes a ground truth ROI attenuation image (cm$^{-1}$) 1302, a reconstructed attenuation image without noise 1304 and a difference 1306. Example 1300 further includes a reconstructed attenuation image with noise added 1308 and a difference compared to the ground truth 1310. Example 1300 further includes a ground truth ROI radio tracer concentration image (MBq/ml) 1312, a reconstructed concentration image without noise 1314 and a difference 1316. Example 1300 further includes a reconstructed radio tracer concentration image with noise added 1318 and a difference compared to the ground truth 1320.

Example 1300 illustrates results of the half-voxel activation scheme for interior SET with the assumption of known line integrals outside the ROI. For the noise-free case, the mean error within the ROI of the attenuation image was 12.66%, while the error within the concentration image was 9.78%. The largest errors are seen at the boundaries of each tracer concentration ring. With Poisson noise added to the measurements, the reconstruction error was 13.49% in the attenuation image and 9.81% in the concentration image.

Generally, the present disclosure provides a holistic system design and mathematical formulation for performing global and interior simultaneous emission-transmission tomography (SET). Example reconstruction results obtained from numerical simulation in both ideal and non-ideal cases demonstrate the imaging capabilities, consistent with several embodiments of the present disclosure. The tissue attenuation and concentration images are determined simultaneously with relatively high accuracy from γ-ray data (i.e., a plurality of selected γ-rays). With noise added, the reconstruction method is able to handle the random variation. It is contemplated that, for interior SET, iterative reconstruction methods may reduce effects from noise and artifacts in the images.

The acquisition method of activating pixels line-by-line demonstrates the feasibility of relatively high accuracy reconstruction in terms of both attenuation coefficients and tracer concentrations. Additionally or alternatively, instead of activating one line of pixels each time, this line may be disabled and the emission of all other pixels may be detected. In this way, only photons from the disabled pixel are "wasted". More generally, the activation and detection scheme can be relatively easily controlled by the gradient magnetic field, and it is contemplated that a more advanced reconstruction method may be designed in the compressed sensing framework. It is contemplated that, by extending the field of view over the entire body surface, nearly all emitted photons may be captured by a cylindrical detector assembly. It is further contemplated that whole-body PET may be adapted for at least one of the SET methods, as described herein, to perform whole-body SPECT-CT in the MRI framework. It is contemplated that such technology may facilitate an increase in image sensitivity, potentially for whole body cancer screening.

It is contemplated that additional or alternative acquisition strategies may be relatively more efficient and effective. In one nonlimiting example, a series of dynamic gradient magnetic fields can be used to modulate polarized signals in a sinusoidal fashion at different frequencies. The measurements may then correspond to results of performing an attenuated Fourier transform, similar to magnetic particle imaging. A sinusoidal excitation method may have a faster acquisition time than pixel-by-pixel activation and may be configured to take the directional emission probability into account as a function of space and time. Relatively more advanced compressed sensing and machine learning techniques may be applied configured to improve the reconstruction quality.

A number of technologies may be utilized to implement the main magnetic field source device 122 of SET device 104 of FIG. 1. In one nonlimiting example, a Helmholtz coil design with a field strength of less than 0.1 T may be utilized. Shimming coils may be utilized to help improve field homogeneity in the imaging region. In another nonlimiting example, superconducting fibers may be utilized configured to achieve a relatively more efficient generation of the magnetic field. These fibers may be constructed with an iron core and fused silica cladding, and are capable of exhibiting superconductivity for an extended period of time after injection with liquid helium. The fiber can be wound into coils to achieve a homogeneous main magnetic field with relatively less power consumption.

Attenuation-based imaging tasks are currently performed with x-rays from an external radiation source, the x-ray tube. In a SET technique, consistent with the present disclosure, polarized radio tracers may be used to serve as internal sources for attenuation-based imaging via γ-rays, which have an energy spectra close to that of x-rays. The internal source of signal means a shorter source-to-detector distance that reduces the attenuation path length, and thus lowers the requisite radiation dose. It is contemplated that this could be an out of box way to perform low-dose CT, as for a given imaging task, relatively fewer photons would be utilized compared to conventional CT methods. It is further contemplated that a system capable of CT-MRI-SPECT may be realized since a SET system, consistent with the present disclosure, may be equipped for MM. This may then enable a higher level synergy relative to two-modality scanners, such as PET-CT, PET-MRI and CT-MRI.

A SET method, apparatus and/or system may be configured to acquire simultaneous emission and transmission data from γ-ray measurements of a polarized radionuclide activated by MRI hardware. A SET method, apparatus and/or system may provide the potential for MR imaging in synchrony. The combined information, co-registered, may provide insight into morphological features and molecular activity in an ROI. Numerical simulation results, described herein, illustrate a relatively accurate reconstruction scheme for global and interior imaging.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Processor circuitry 112 may include, but is not limited to, a single core processing unit, a multicore processor, a graphics processing unit, a microcontroller, an application-specific integrated circuit (ASIC), a field programmable gate array (FPGA), a programmable logic device (PLD), etc.

Memory circuitry 114 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory circuitry 114 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. A method of multimodality imaging, the method comprising:
   reconstructing, by a simultaneous emission transmission (SET) circuitry, a concentration image based, at least in part, on a plurality of selected γ-rays; and
   reconstructing, by the SET circuitry, an attenuation image based, at least in part, on the plurality of selected γ-rays, the plurality of selected γ-rays emitted by a polarized radio tracer included in a test object, the selected γ-rays selected based, at least in part, on a radio frequency (RF) pulse and based, at least in part, on a gradient magnetic field.

2. The method of claim 1, further comprising:
   providing, by a main magnetic field source device, a uniform main magnetic field to the test object;
   adjusting, by a gradient magnetic field device, the main magnetic field to yield the gradient magnetic field; and
   providing, by RF source circuitry, the RF pulse to the test object.

3. The method of claim 2, wherein the adjusting is configured to select γ-rays emitted from a location with pixel resolution.

4. The method of claim 2, wherein the adjusting is configured to select γ-rays emitted from a location with a fraction of a pixel resolution.

5. The method of claim 2, wherein the main magnetic field source device is stationary.

6. The method of claim 2, wherein the main magnetic field source device is configured to rotate about the test object.

7. The method of claim 1, wherein the reconstructed images correspond to the entire test object.

8. The method of claim 1, wherein the reconstructed images correspond to a region of interest included in the test object.

9. The method of claim 8, wherein the reconstructing is based, at least in part, on a known tracer concentration at a reference point pixel.

10. An SET device configured for performing the method according to claim 1, the SET device comprising a main magnetic field source, a gradient magnetic field source, and an RF source.

11. A non-transitory computer readable storage device having stored thereon instructions that when executed by one or more processors result in the following operations comprising the method according to claim 1.

12. A simultaneous emission transmission (SET) system comprising:
- a SET circuitry configured to reconstruct a concentration image based, at least in part, on a plurality of selected γ-rays and to reconstruct an attenuation image based, at least in part, on the plurality of selected γ-rays,
- the plurality of selected γ-rays emitted by a polarized radio tracer included in a test object, the selected γ-rays selected based, at least in part, on a radio frequency (RF) pulse and based, at least in part, on a gradient magnetic field.

13. The system of claim 12, further comprising:
- a main magnetic field source device configured to provide a uniform main magnetic field to the test object;
- a gradient magnetic field device configured to adjust the main magnetic field to yield the gradient magnetic field; and
- an RF source circuitry configured to provide the RF pulse to the test object.

14. The system of claim 13, wherein the adjusting is configured to select g-rays emitted from a location with pixel resolution.

15. The system of claim 13, wherein the adjusting is configured to select g-rays emitted from a location with a fraction of a pixel resolution.

16. The system of claim 13, wherein the main magnetic field source device is stationary.

17. The system of claim 13, wherein the main magnetic field source device is configured to rotate about the test object.

18. The system of claim 12, wherein the reconstructed images correspond to the entire test object.

19. The system of claim 12, wherein the reconstructed images correspond to a region of interest included in the test object.

20. The system of claim 19, wherein the reconstructing is based, at least in part, on a known tracer concentration at a reference point pixel.

* * * * *